Figure 4:
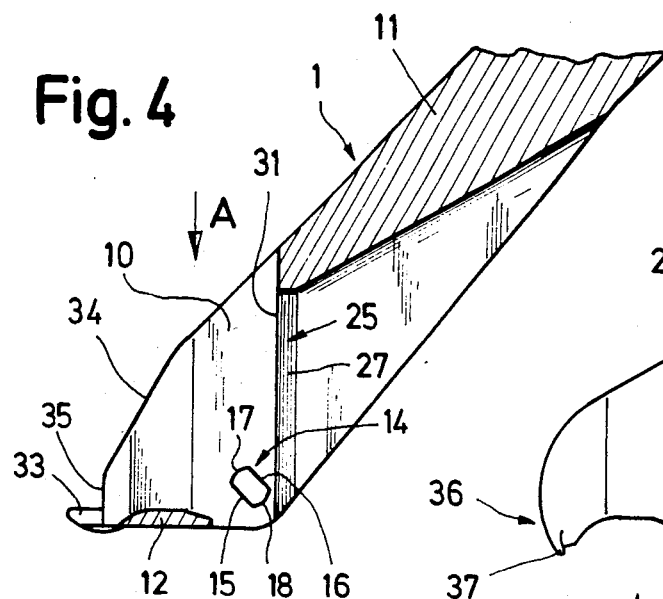

United States Patent [19]

Braun

[11] Patent Number: 4,569,505
[45] Date of Patent: Feb. 11, 1986

[54] CLIP REMOVING FORCEPS

[75] Inventor: Karl Braun, Talheim, Fed. Rep. of Germany

[73] Assignee: Aesculap-Werke AG, Tuttlingen, Fed. Rep. of Germany

[21] Appl. No.: 624,675

[22] PCT Filed: Oct. 14, 1983

[86] PCT No.: PCT/EP83/00269
§ 371 Date: Jun. 21, 1984
§ 102(e) Date: Jun. 21, 1984

[87] PCT Pub. No.: WO84/01500
PCT Pub. Date: Apr. 26, 1984

[30] Foreign Application Priority Data

Oct. 21, 1982 [DE] Fed. Rep. of Germany ....... 3238898

[51] Int. Cl.⁴ .......................................... B25C 11/00
[52] U.S. Cl. .................................................. 254/28
[58] Field of Search .................. 254/18; 128/321, 323; 227/63; 16/225, DIG. 13

[56] References Cited

U.S. PATENT DOCUMENTS 1,423,866  7/1922  Miller .
2,202,984  3/1939  Drypolcher .
2,762,604  1/1953  Misson .
4,026,520  5/1977  Rothfuss et al. .
4,487,394 12/1984  Rothfuss et al. ..................... 254/28

FOREIGN PATENT DOCUMENTS 1709628  5/1955  Fed. Rep. of Germany .
186088  11/1936  Switzerland .
1172307 11/1967  United Kingdom .

Primary Examiner—Robert C. Watson
Attorney, Agent, or Firm—Kenway & Jenney

[57] ABSTRACT

In order to simplify production of clip removing forceps used to bend open skin clips, it is suggested that one of the two branch elements encircles the other in the shape of a U in the region of pivotal connection, that one of the two branch elements bears on its side walls facing the other branch element projections arranged at the axis of rotation, that the other branch element has circular recesses to accommodate these projections, that the projections have a circular cross section corresponding to that of the recesses, whereby two opposite side faces of these projections are flattened, and that a groove runs from the circular recess to the edge of the other branch element, the width of this groove corresponding at least to the distance between the flattened sides of the projections but being smaller than the diameter of the circular recess and this groove being aligned such that, in the operating position of the two branch elements, the curved side portions of the projections rest at least partially on cylindrical side walls of the recess.

11 Claims, 17 Drawing Figures

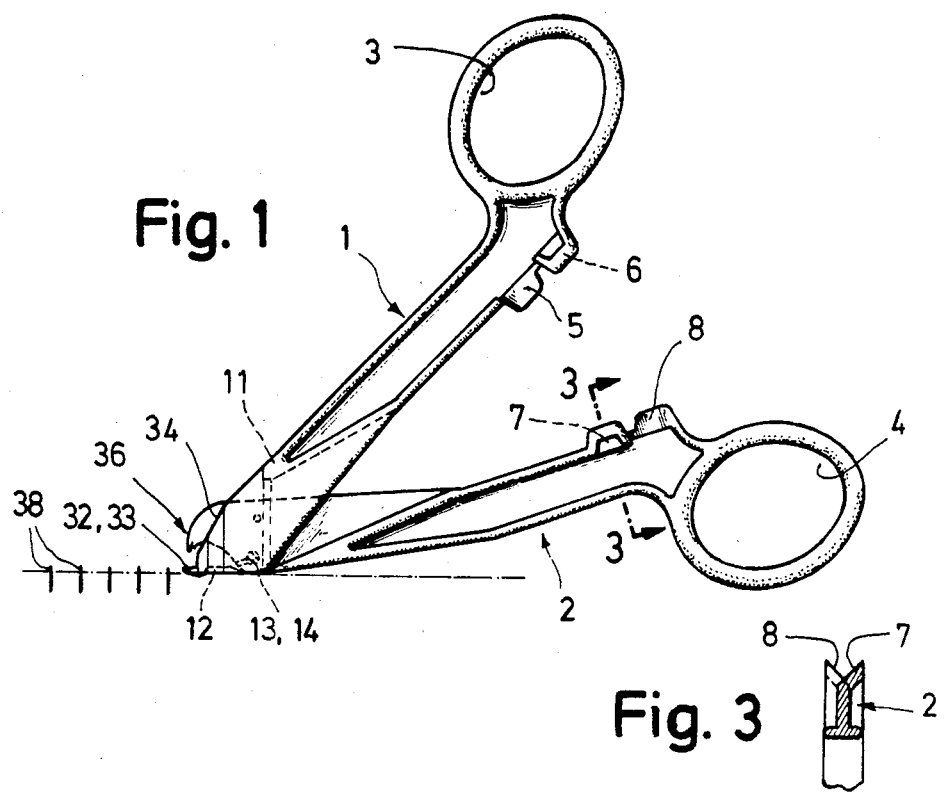
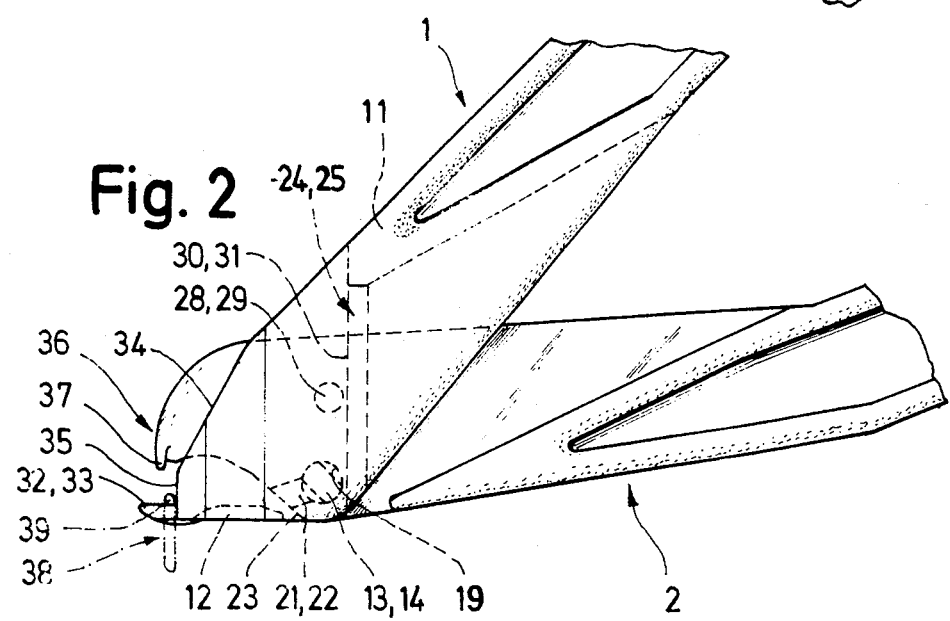

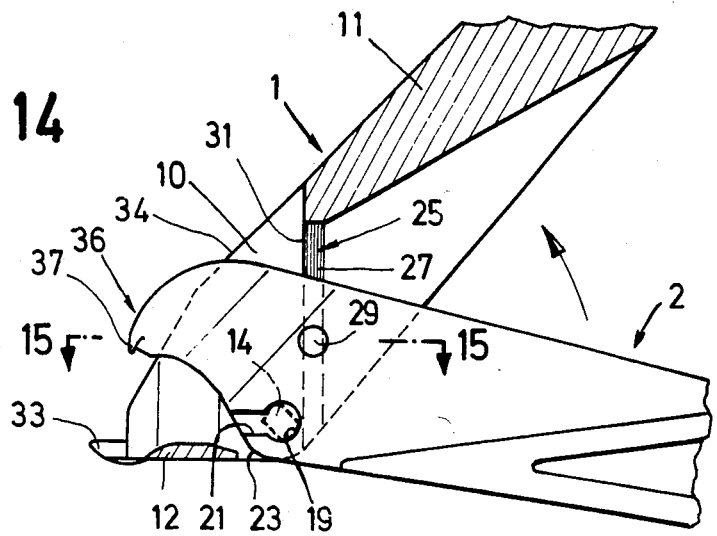
Fig. 14
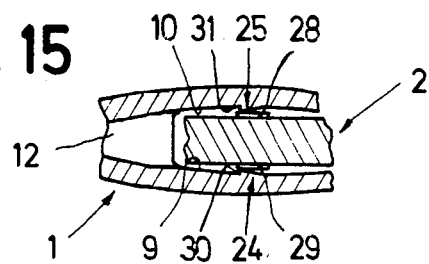
Fig. 15
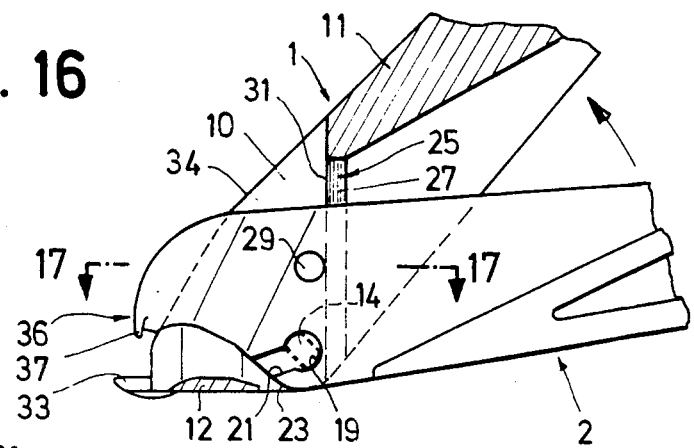
Fig. 16
Fig. 17
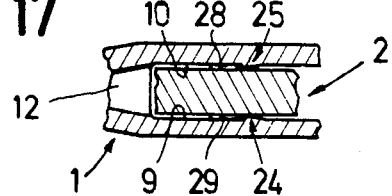

CLIP REMOVING FORCEPS

The invention relates to a clip removing forceps for bending open skin clips, comprising two branch elements pivotally joined together, one of which has at its free end two parallel anvils which are insertable between the skin and the crown of the clip to be bent open, and also comprising a bending punch at the free end of the other branch element, said bending punch dipping between the two anvils when the branch elements are pivoted together.

Clip removing forceps of this type are preferably made of metal and serve to bend open the skin clips used to hold the edges of a wound together and remove them from their position once the wound has healed.

Normally, the two branch or handle elements of such a clip removing forceps are pivotally joined by a hinge pin, e.g. by a screw or rivet. Such an arrangement is complicated and expensive to produce as at least three parts have to be joined together.

The object of the invention is to improve a clip removing forceps of this type such that it is simpler to manufacture, in particular with the aim of designing such clip removing forceps as disposable articles.

With regard to a clip removing forceps of the type described above, this object is accomplished according to the invention in that one of the two branch elements encircles the other branch element in the shape of a U in the region of pivotal connection, that one of the two branch elements bears on its side walls facing the other branch element projections arranged at the axis of rotation, that the other branch element has circular recesses for receiving the projections, that these projections have a circular cross section corresponding to that of the recesses, whereby two opposite sides of the projections are flattened, and that a groove runs from each circular recess to the edge of the other branch element, the width of this groove corresponding at least to the distance between the flattened sides of the projections but being smaller than the diameter of the circular recesses, and this groove being aligned such that in the operating position of the two branch elements the curved side portions of the projections rest at least partially on the cylindrical side walls of the recesses.

This arrangement enables the two branch elements to be pivotally connected directly with each other without separate parts, such as hinge pins etc., being necessary. It is sufficient for the two branch elements to be fitted together such that the flattened projections slide along the grooves in the other branch element and into the recesses. The branch elements are subsequently pivoted into their operating position. The curved portions of the projections are thereby guided exactly in the recesses with their circular cross section.

It is advantageous for the groove to have the same depth as the recess but the recesses may also be formed by a single throughbore.

The groove and the flattened portions of the projections are preferably oriented such that the projections may be inserted into the groove only when the branch elements for between them a greater angular aperture than that occurring during operation.

In a preferred embodiment, both branch elements have locking projections on their side faces facing each other, these locking projections sliding past each other when the branch elements are closed from their fitting position into their operating position and preventing any return movement from the operating position into the fitting position. This ensures that the branch elements cannot be detached from each other once they have been assembled. It is sufficient to slide one branch element into the other in the direction of the grooves in this other branch element and, subsequently, to close the two branch elements. The two locking projections thereby slide past each other until the clip removing forceps is in its operating position, i.e. in a position in the region between the normal open position and the closed position.

It is advantageous for at least one of the two locking projections to have an inclined sliding surface for the other locking projection which increasingly spaces the two side faces of the branch elements from each other during closing. This makes it easier for the locking projections to slide past each other when the two branch elements are pivoted into their operating position.

It is also possible for one locking projection to be conical in design and the other linear.

In another preferred embodiment, two guide faces are arranged at the grip end of one branch element on its side facing the other branch element, these guide faces being inclined relative to the plane defined by the two branch elements. The other branch element has two complementary guide faces which abut on the guide faces of the first branch element when the branch elements are closed. These guide faces ensure that when the two branch elements are being closed they are guided exactly in the plane of the instrument defined by these two branch elements and that any lateral bending of the branch elements, during closing, is avoided.

It is particularly advantageous for the two guide faces of each branch element to be offset against each other in the longitudinal direction of the branch elements. This means that when the branch elements have the same width the two guide faces will have a greater length and guidance or alignment is therefore ensured through a greater angle.

In a preferred embodiment, a downwardly extending projection is arranged on the bending punch, this projection embracing the crown of the clip when the branch elements are closed and pressing it against a stop face which adjoins the end of the anvils facing the branch elements. This ensures that the clips always rest directly on the ends of the anvils adjacent the branch elements. The bending moment exerted on the anvils when the clips are bent open is then kept to a minimum.

It is favourable to have the stop face extending perpendicular to the longitudinal direction of the anvils.

Each of the branch elements is preferably designed as a one-piece plastic part.

Figure 6:
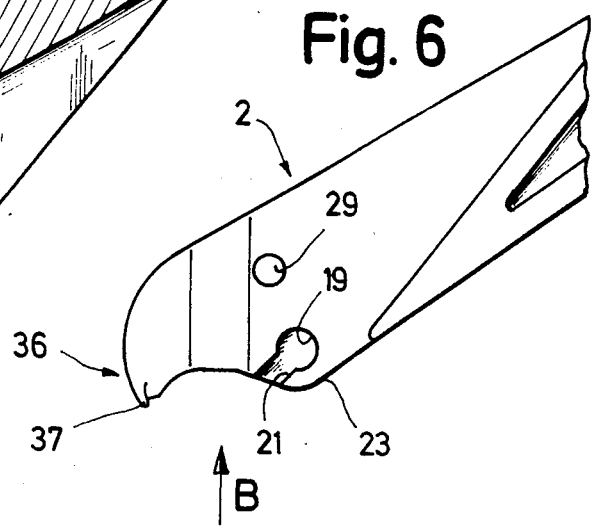
Figure 5:
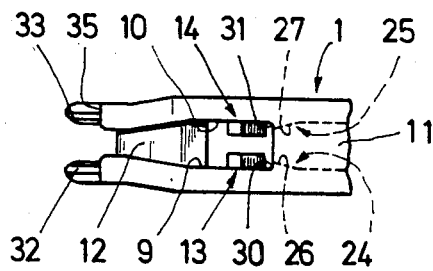
Figure 7:
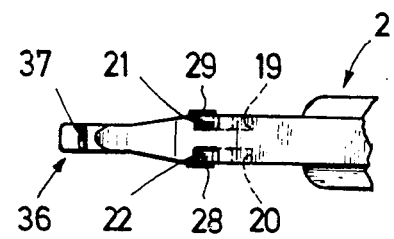
Figure 8:
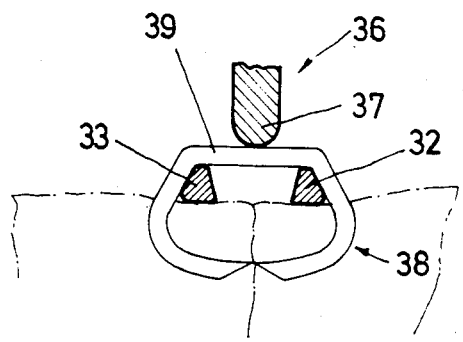
Figure 9:
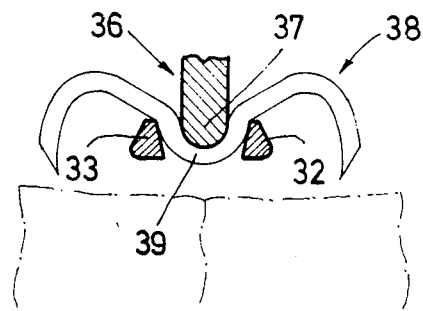
Figure 10:
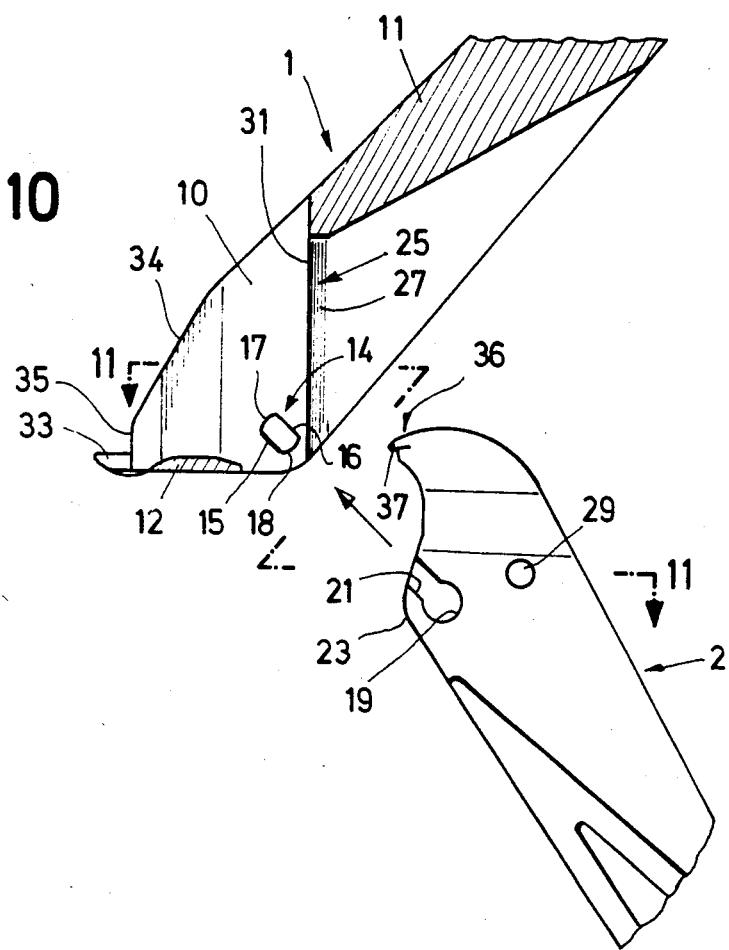
Figure 11:
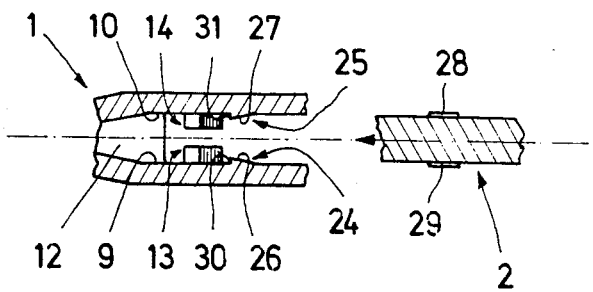
Figure 12:
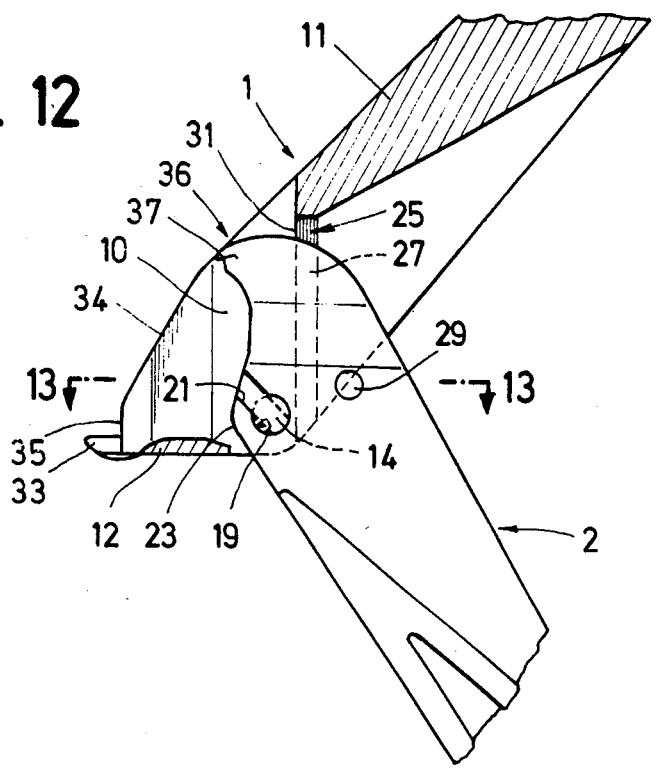
Figure 13:
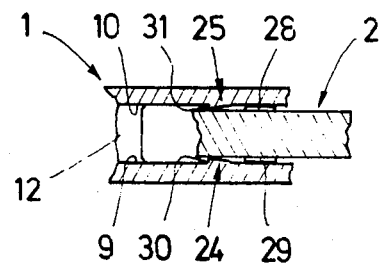

The following description of preferred embodiments of the invention serves to explain the invention in greater detail, in conjunction with the drawings which show:

FIG. 1: a side view of a clip removing forceps;

FIG. 2: an enlarged partial side view of the bending region of the clip removing forceps of FIG. 1;

FIG. 3: a sectional view along line 3—3 in FIG. 1;

FIG. 4: a partial, longitudinal sectional view of one of the two branch elements of the clip removing forceps of FIG. 1;

FIG. 5: a view in the direction of arrow A in FIG. 4;

FIG. 6: a partial side view of the other branch element of the clip removing forceps of FIG. 1;

FIG. 7: a view in the direction of arrow B in FIG. 6;

FIG. 8: a cross sectional view through the bending punch and anvils of a clip removing forceps prior to a skin clip being bent open;

FIG. 9: a view similar to FIG. 8 after the skin clip has been bent open;

FIG. 10: a view of the front region of the forceps prior to assembly of the two branch elements;

FIG. 11: a sectional view along line 11—11 in FIG. 10;

FIG. 12: a view similar to FIG. 10 showing insertion of the projecting of one branch element into the recess of the other branch element;

FIG. 13: a sectional view along line 13—13 in FIG. 12;

FIG. 14: a view similar to FIG. 10 showing the two locking projections sliding past each other;

FIG. 15: a sectional view along line 15—15 in FIG. 14;

FIG. 16: a view similar to FIG. 10 of the forceps in their operating position and FIG. 17: a sectional view along line 17—17 in FIG. 16.

The clip removing forceps illustrated in the drawings has two branch or handle elements 1 and 2 which are pivotally connected to each other, like pliers or scissors, near one end of the two branch elements. At their other ends, these branch elements have finger apertures 3 and 4, like a pair of scissors. In addition, the inner facing sides of the two branch elements are each provided with two guide faces 5 and 6 or 7 and 8, each pair being offset against each other in the longitudinal direction of the branch elements. All these guide faces are inclined relative to the plane described by the two branch elements. In this respect, the staggered guide faces of one branch element are each inclined in opposite directions. The corresponding guide faces of the other branch element are inclined so as to be complementary to the guide faces of the opposite branch element. When the branch elements are closed, the guide faces engage each other in pairs 5 and 7 and 6 and 8 and secure the two branch elements against any displacement out of the plane defined by these branch elements. This allows the pivot mounting between the two branch elements to be of a less rigid design. This is a particular advantage when the two branch elements, as preferably provided, are each produced in one piece from plastics material.

The first branch element 1 has a U-shaped cross section in the region of the pivot mounting, i.e. it has, in this region, two parallel side walls 9 and 10 connected via a web-like bulge 11 in the branch element 1. A further connection is provided in the direct vicinity of the free end of both side walls via a web 12.

Each side wall 9 or 10 is provided with an inwardly directed projection 13 or 14, which has a substantially circular cross section. These projections are, however, flattened on opposite sides to form two parallel side faces 15 and 16 which are connected by circular-cylindrical portions 17 and 18 (FIG. 4). The plane side faces 15 and 16 extend substantially perpendicular to the longitudinal direction of the branch element.

The width of the other branch element 2 in the region of the pivot mounting is less than the inside breadth of the two side walls 9 and 10 of branch element 1. This branch element 2 has, on both sides, recesses 19 and 20 which have a circular cross section and a diameter which is slightly larger than the diameter of the curved portions 17 and 18 of projections 13 or 14. A groove 21 or 22 leads from each recess 19 and 20 to the edge 23 of the branch element 2. The width of both grooves is slightly greater than the distance between the parallel side faces 15 and 16 of projections 13 or 14 but smaller than the diameter of recesses 19 and 20. The grooves extend substantially parallel to the longitudinal direction of branch element 2.

The depth of grooves 21 and 22 may be less than that of recesses 19 and 20 but the grooves and recesses have, preferably, the same depth. The recesses may also be formed by a single throughbore.

The inner side of each of the two side walls 9 and 10 of branch element 1 also has a ridge-like locking projection 24 or 25 which extends from the web-like bulge 11 to the edge of branch element 1 and has a cross section shaped like a saw tooth. The inclined guide faces 26 and 27 of these projections thereby converge towards the free end of the branch element (FIG. 11).

In the pivot region, the branch element 2 has, on each side, a conical projection 28 or 29 which cooperates with the locking projections 24 and 25 on the other branch element, as described in the following.

Both branch elements are preferably manufactured as one-piece plastic parts and may be pivotally connected, due to the design described, simply by being fitted together. The steps required for this are illustrated in FIGS. 10 to 17.

First of all, the branch element 2 is brought towards branch element 1 in a direction substantially perpendicular to branch element 1. Its free end is inserted between the two side walls 9 and 10 such that the parallel side faces 15 and 16 of the projections 13 and 14 may be inserted into the grooves 21 and 22 of branch element 2 (FIGS. 10 and 11). The projections 13 and 14 finally enter the recesses 19 and 20. In this position, the locking projections 28 and 29 of branch element 2 are still located on the side of the bar-shaped locking projections 24 and 25 facing towards the finger apertures (FIGS. 12 and 13).

When the two branch elements are pivoted into their closed position, the projections 13 and 14 turn in the recesses 19 and 20 such that the side faces 15 and 16 of projections 13 and 14 are no longer parallel to grooves 21 and 22 and the projections may no longer move back into the grooves from the recesses even when the branch elements are moved relative to each other. At the same time, the locking projections 28 and 29 slide over the sliding surfaces 26 and 27 and beyond the locking projections 24 and 25 (FIGS. 14 and 15), thereby bending the side walls 9 and 10 flexibly apart.

As soon as the locking projections 28 and 29 have moved past the locking projections 24 and 25, the clip removing forceps is in its operating position. It is not possible for any return movement to take place as the locking projections 28 and 29 abut on stop faces 30 and 31 of locking projections 24 and 25 which extend perpendicular to the side walls 9 and 10 (FIGS. 16 and 17). The two branch elements are now permanently connected for pivotal movement relative to each other.

At its free end, each side wall 9 and 10 of branch element 1 bears an anvil 32 or 33 which extends substantially parallel to the lower edge of branch element 1. At the point of connection of the two anvils to branch element 1, the upper edge 34 of branch element 1 extends perpendicular to its lower edge and forms a stop face 35 which extends perpendicular to the longitudinal direction of the anvils (FIGS. 2).

Branch element 2 is designed at its free end to form a bending punch 36 and bears a downwardly directed projection 37. The distance between this projection and the stop faces 35 corresponds approximately to the wire gauge of the skin clip 38 (FIG. 2).

In order to bend the skin clips open, the two anvils of the clip removing forceps are moved, in the manner illustrated in FIG. 1, under a skin clip 38, these two anvils thereby engaging on the underside of the crown 39 of the skin clip 38 in the manner shown in FIG. 8. When the two branch elements are closed, the bending punch 36 presses downwards onto the crown 39 and bends the skin clip into its open position (FIG. 9). The projection 37 on the underside of the bending punch 36 thereby ensures that the crown 39 of the skin clip 38 is pressed against the stop faces 35, i.e. the skin clip is supported by the anvils in the region of their point of connection to branch element 1 so that the bending moment exerted by the bending punch on the anvils, through the crown 39 of skin clip 38, is reduced to a minimum value as the lever arm of the anvils is shortened.

The clip removing forceps described above consists of only two individual parts which may be manufactured in the simplest possible manner. Both parts may be pivotally connected with each other without difficulty, as described. This connection may also be permanent. This simplified production considerably reduces production costs, which means that the clip removing forceps may be designed as a disposable article in the interests of sterile operation.

What is claimed is:

1. Clip removing forceps for bending open skin clips, comprising two branch elements pivotally joined together, one of which has at its free end two parallel anvils which are insertable between the skin and the crown of the clip to be bent open, and also comprising a bending punch at the free end of the other branch element, said bending punch dipping between the two anvils when the branch elements are pivoted together, characterized in that one of said two branch elements (1) encircles the other branch element in the shape of a U in the region of pivotal connection, that one of said two branch elements (1 or 2) bears on its side walls facing said other branch element projections (13, 14) arranged at the axis of rotation, that the other branch element (2 or 1) has circular recesses (19, 20) for receiving said projections (13 or 14), that said projections (13, 14) have a circular cross section corresponding to that of said recesses (19 or 20), whereby two opposite side faces (15, 16) of said projections are flattened, and that a groove (21 or 22) runs from each circular recess (19, 20) to the edge (23) of said other branch element (2 or 1), the width of said groove corresponding at least to the distance between the side faces (15, 16) of the projections (13 or 14) but being smaller than the diameter of the circular recesses (19 or 20), and said groove being aligned such that in the operating position of said two branch elements (1, 2) curved portions (17, 18) of said projections (13, 14) rest at least partially on the cylindrical side walls of said recesses (19, 20).

2. Forceps as defined in claim 1, characterized in that the grooves (21, 22) are of the same depth as the recesses (19 or 20).

3. Forceps as defined in claims 1 or 2, characterized in that the grooves (21, 22) and the side faces (15, 16) of the projections (13 or 14) are oriented such that the projections slide into the grooves only when the branch elements (1, 2) form between them a greater angular aperture than that occurring during operation.

4. Forceps as defined in claim 1, characterized in that both branch elements (1, 2) have locking projections (24, 25 or 28, 29) on their side faces facing each other, said locking projections sliding past each other when the branch elements are closed from their fitting position into their operating position and preventing any return movement from the operating position into the fitting position.

5. Forceps as defined in claim 4, characterized in that at least one of said two locking projections (24, 25) has an inclined sliding surface (26 or 27) for the other locking projection (28 or 29), which increasingly spaces the two side faces of the branch elements (1, 2) from each other during closing.

6. Forceps as defined in one of claims 4 or 5, characterized in that one locking projection (28, 29) is conical in design and the other linear.

7. Forceps as defined in claim 1 characterized in that two guide faces (5, 6) are arranged at the grip end of one branch element (1) on its side facing towards the other branch element, said guide faces being inclined relative to the plane determined by said two branch elements (1, 2), and that the other branch element has two complementary guides faces (7, 8) which engage on the guide faces (5, 6) of said first branch element when said branch elements (1, 2) are closed.

8. Forceps as defined in claim 7, characterized in that the two guide faces (5, 6 or 7, 8) of each branch element (1 or 2) are offset against each other in the longitudinal direction of said branch elements.

9. Forceps as defined in claim 1 characterized in that a downwardly extending projection (37) is arranged on the bending punch (36), said projection embracing the crown (39) of the clip (38) when the branch elements (1, 2) close and pressing it against a stop face (35) which adjoins the end of the anvils (32, 33) toward the branch elements.

10. Forceps as defined in claim 9, characterized in that the stop face (35) extends perpendicular to the longitudinal direction of the anvils (32, 33).

11. Forceps as defined in claim 1 characterized in that each of the two branch elements (1, 2) is designed as a one-piece plastic part.

* * * * *